US007820389B2

(12) United States Patent
Shi

(10) Patent No.: US 7,820,389 B2

(45) Date of Patent: Oct. 26, 2010

(54) INHIBITION OF MISMATCH HYBRIDIZATION BY A UNIVERSAL COMPETITOR DNA

(75) Inventor: Chunnian Shi, San Diego, CA (US)

(73) Assignee: Geneohm Sciences, Inc., San Diego, CA (US)

(*) Notice: Subject to any disclaimer, the term of this patent is extended or adjusted under 35 U.S.C. 154(b) by 0 days.

(21) Appl. No.: 11/969,718

(22) Filed: Jan. 4, 2008

(65) Prior Publication Data

US 2008/0188005 A1 Aug. 7, 2008

Related U.S. Application Data

(60) Provisional application No. 60/884,341, filed on Jan. 10, 2007.

(51) Int. Cl.
*C12Q 1/68* (2006.01)
*C07H 21/02* (2006.01)
*C07H 21/04* (2006.01)

(52) U.S. Cl. .......................... 435/6; 536/23.1; 536/24.3

(58) Field of Classification Search ..................... 435/6; 536/23.1, 24.3
See application file for complete search history.

(56) References Cited

U.S. PATENT DOCUMENTS 4,469,863 A 9/1984 Ts'o et al.
4,683,195 A 7/1987 Mullis et al.
4,683,202 A 7/1987 Mullis
5,034,506 A 7/1991 Summerton et al.
5,216,141 A 6/1993 Benner
5,235,033 A 8/1993 Summerton et al.
5,312,527 A 5/1994 Mikkelsen et al.
5,386,023 A 1/1995 Sanghvi et al.
5,447,841 A 9/1995 Gray et al.
5,602,240 A 2/1997 Mesmaeker et al.
5,644,048 A 7/1997 Yau
5,776,672 A 7/1998 Hashimoto et al.
5,851,772 A * 12/1998 Mirzabekov et al. ........... 435/6
5,972,692 A 10/1999 Hashimoto et al.
5,985,549 A * 11/1999 Singer et al. ................... 435/6
6,200,761 B1 3/2001 Meade et al.
6,221,586 B1 4/2001 Barton et al.
7,258,978 B2 8/2007 Crothers et al.
7,375,198 B2 * 5/2008 McGall et al. ............. 536/23.1
2002/0164596 A1 * 11/2002 Weimer ......................... 435/6
2003/0064382 A1 * 4/2003 Preparata et al. ............... 435/6
2003/0124521 A1 * 7/2003 Coull et al. .................... 435/6
2004/0086895 A1 5/2004 Crothers et al.
2004/0219565 A1 * 11/2004 Kauppinen et al. ............. 435/6
2005/0118616 A1 6/2005 Kawashima et al.
2005/0164184 A1 * 7/2005 Chun ........................... 435/6
2005/0191646 A1 * 9/2005 Lockhart et al. ............... 435/6
2007/0003938 A1 * 1/2007 Fu et al. ........................ 435/6
2007/0141610 A1 * 6/2007 Spier ............................ 435/6
2008/0286775 A1 * 11/2008 Becker et al. .................. 435/6

FOREIGN PATENT DOCUMENTS

EP 0 304 184 A1 2/1989
EP 1 683 872 A1 7/2006
WO WO 98/24933 A1 6/1998
WO WO 03/027328 A3 4/2003

OTHER PUBLICATIONS

Martin et al, Nucleic Acids Research, vol. 13, pp. 8927-8938 (1985).*
Ohtsuka et al., J. Biol. Chem. 260 : 2605-08 (1985).*
Zon et al., Nucleic Acids Research 13(22) : 8181-8196 (1985).*
Loakes et al., Nucleosides and Nucleotides 14:1001-1003 (1995).*
Neuner et al., Nucleic Acids Research 26( 2 ): 576-581 (1998).*
Crawford-Miksza et al. J of Clinical Microbiology, 37:1107-1112 (1999).*
Amosova et al., "Effect of the 1-(2'-deoxy-beta-D-ribofuranosyl)-3-nitropyrrole residue on the stability of DNA duplexes and triplexes", *Nucl. Acids. Res.* (1997) 25(10):1930-1934.
Bains, "Characterizing and sequencing cDNAs using oligonucleotide hybridization", *DNA Seq.* (1993) 4(3):143-150.
Bergstrom et al., "Comparison of the base pairing properties of a series of nitroazole nucleobase analogs in the oligodeoxyribonucleotide sequence 5'-d(CGCXAATTYGCG)-3", *Nucl. Acids. Res.* (1997) 25:1935-1942.
Bergstrom et al., "Synthesis, Structure, and Deoxyribonucleic Acid Sequencing with a Universal Nucleoside: 1-(2'-Deoxy-.beta.-D-ribofuranosyl)-3-nitropyrrole." *J. Am. Chem. Soc.* (1995) 117:1201-1209.
Dempcy et al., "Synthesis of a thymidyl pentamer of deoxyribonucleic guanidine and binding studies with DNA homopolynucleotides", *Proc. Natl. Acad. Sci. USA* (1995) 92(13):6097-6101.
Drmanac et al., "DNA sequence determination by hybridization: a strategy for efficient large-scale sequencing", *Science* (1993) 260(5114):1649-1652.
Eckstein et al. Oligonucleotides and Analogues: A Practical Approach. (1991). [Table of Contents Only].
Guo et al., "Enhanced discrimination of single nucleotide polymorphisms by artificial mismatch hybridization", *Nature Biotechnology* (1997) 15(4):331-335.
International Search Report for International Application No. PCT/US2008/050530, dated Jul. 24, 2008.
Keller et al., DNA Probes *Stockton Press* 2nd Ed. (1993). [Table of Contents Only].
Kennell, "Principles and practices of nucleic acid hybridization", *Prog. Nucleic Acid Res. Mol. Biol.* (1971) 11:259-301.
Letsinger et al. "Cationic oligonucleotides", *J. Am. Chem. Soc.* (1988) 110:4470-4471.

(Continued)

*Primary Examiner*—Ethan Whisenant
(74) *Attorney, Agent, or Firm*—Knobbe Martens Olson & Bear LLP

(57) ABSTRACT

Provided herein are compositions and methods for enhancing the relative efficiency of hybridization between target nucleic acids and capture probes compared to target variants and capture probes.

34 Claims, 7 Drawing Sheets

OTHER PUBLICATIONS

Letsinger et al., "Effects of pendant groups at phosphorus on binding properties of d-ApA analogues", *Nucl. Acids Res.* (1986) 14(8):3487-3499.

Letsinger et al. "Hybridization of Alternating Cationic/Anionic Oligonucleotides to RNA Segments." *Nucleoside & Nucleotide* (1994) 13:1597-1605.

Letsinger, "Phosphoramidate analogs of oligonucleotides", *J. Org. Chem.* (1970) 35(11):3800-3803.

Loakes et al., "3-Nitropyrrole and 5-nitroindole as universal bases in primers for DNA sequencing and PCR", *Nucl. Acids Res.* (1995) 23(13):2361-2366.

Loakes et al., "5-Nitroindole as an universal base analogue", *Nucl. Acids Res.* (1994) 22(20):4039-4043.

Loakes, "Survey and summary: The applications of universal DNA base analogues", *Nucl. Acids Research* (2001) 29(12):2437-2447.

Mag et al., "Synthesis and selective cleavage of an oligodeoxynucleotide containing a bridged internucleotide 5'-phosphorothioate linkage", *Nucl. Acids Res.* (1991) 19(7):1437-1441.

Martin et al., "Base pairing involving deoxyinosine: implications for probe design", *Nucl. Acids Res.* (1985) 13(24):8927-8938.

Millican et al., "Synthesis and biophysical studies of short oligodeoxynucleotides with novel modifications: a possible approach to the problem of mixed base oligodeoxynucleotide synthesis", *Nucl. Acids Res.* (1984) 12(19):7435-7453.

Milligan et al., "Current concepts in antisense drug design", *J. Med. Chem.* (1993) 36(14):1923-1937.

Nichols et al., "A universal nucleoside for use at ambiguous sites in DNA primers", *Nature* (1994) 369(6480):492-493.

Nielsen, "PNA hybridizes to complementary oligonucleotides obeying the Watson-Crick hydrogen-bonding rules", *Nature* (1993) 365(6446):566-568.

Ogawa et al., "Efforts toward the expansion of the genetic alphabet information storage and replication with unnatural hydrophobic base pairs", *J. Am. Chem. Soc.* (2000) 122:3274-3287.

Pauwels et al., "Biological-activity of new 2-5a analogs", *Chimica Scripta* (1986) 26: 141-145.

Rawls, Rebecca. "Optimistic about antisense: promising clinical results and chemical strategies for further improvements delight antisense drug researchers", *C & E News* dated Jun. 2, 1997, p. 35.

Rohrwild et al., "Inosine-containing primers for mRNA differential display", *Trends in Genetics* (1995) 11(8):300.

Sambrook et al., *Molecular Cloning: A Laboratory Manual 2nd Ed.* Cold Spring Harbor Laboratory Press (1989). [Table of Contents Only].

Sawai, Hiroaki. "Synthesis and properties of oligoadenylic acids containing 2'-5' phosphoramide linkage", *Chem. Lett.* (1984) p. 805-808.

Schweitzer et al. "Hydrophobic, Non-Hydrogen-Bonding Bases and Base Pairs in DNA." *J. Am. Chem. Soc.* (1995) 117:1863-1872.

Seela et al. "7-Deaza-2'-Deoxyinosine: A Stable Nucleoside With the Ambiguous Base Pairing Properties of 2'-Deoxyinosine." *Nucleosides & cleotides* (1999) 18:425-441.

Sprinzl et al., "Enzymatic incorporation of ATP and CTP analogues into the 3' end of tRNA", *Eur. J. Biochem.* (1977) 81(3):579-589.

Van Aerschot et al., "An acyclic 5-nitroindazole nucleoside analogue as ambiguous nucleoside", *Nucl. Acids. Res.* (1995) 23(21):4363-4370.

Young et al., "Efficient isolation of genes by using antibody probes", *Proc. Nat. Acad. Sci. USA* (1983) 80(5):1194-1198.

Zhang et al., "Exploratory studies on azole carboxamides as nucleobase analogs: thermal denaturation studies on oligodeoxyribonucleotide duplexes containing pyrrole-3-carboxamide", *Nucl. Acids Res.* (1998) 26(9):2208-2215.

* cited by examiner

Change of 10 A Linker to COAG C1 Has Little effect on Responses in Detection

Oneway Analysis of 10 A vs. C

Missing Rows 28

Means and Std Deviations

| Level | Number | Mean | Std Dev | Std Err Mean | Lower 95% | Upper 95% |
|---|---|---|---|---|---|---|
| !0 A | 12 | 1352.48 | 83.232 | 24.027 | 1299.6 | 1405.4 |
| C1 | 12 | 1413.94 | 109.291 | 31.550 | 1344.5 | 1483.4 |

- **Amplicon: 1:1 dilution of *glabrata* in 3xSSC/0.05%Tween 20**
- Hybr.: 20'a t 58-59 $^{0}$C VWR oven

Amplicon: *gulliermondii*
TG mismatch

Where: M: Match
MM: A single base pair mismatch

Means and Std Deviations

| Level | Number | Mean | Std Dev | Std Err Mean | Lower 95% | Upper 95% |
|---|---|---|---|---|---|---|
| 0.8x M | 6 | 480.68 | 57.210 | 23.356 | 421 | 540.7 |
| 0.8x MM | 6 | 12.77 | 12.781 | 5.218 | -0.6446 | 26.2 |
| Match - | 10 | 1706.06 | 108.189 | 34.212 | 1629 | 1783.5 |
| MM - | 10 | 152.57 | 51.543 | 16.299 | 116 | 189.4 |
| Match + | 10 | 1499.32 | 114.390 | 36.173 | 1417 | 1581.1 |
| MM + | 10 | 33.27 | 16.429 | 5.195 | 22 | 45.0 |

Effect: Mismatch currents: From 152 nA to 33 nA

AC mismatch
Amplicon: *tropicalis* 3x

Means and Std Deviations

| Level | Number | Mean | Std Dev | Std Err Mean | Lower 95% | Upper 95% |
|---|---|---|---|---|---|---|
| M/0.8 | 10 | 183.57 | 48.246 | 15.257 | 149.1 | 218.1 |
| MM/0.8 | 10 | 25.18 | 9.461 | 2.992 | 18.4 | 31.9 |
| M/3x/0 uM | 8 | 1423.16 | 123.563 | 43.686 | 1319.9 | 1526.5 |
| MM/3x/0 uM | 8 | 202.94 | 41.925 | 14.823 | 167.9 | 238.0 |
| M/3x/2 uM | 12 | 1230.40 | 71.345 | 20.595 | 1185.1 | 1275.7 |
| MM/3x/2 uM | 12 | 48.35 | 11.635 | 3.359 | 41.0 | 55.7 |

Effect: Mismatch currents: From 202 nA to 48 nA

Amplicon: *glabrata*
CT mismatch

Means and Std Deviations

| Level | Number | Mean | Std Dev | Std Err Mean | Lower 95% | Upper 95% |
|---|---|---|---|---|---|---|
| [15.1-3I]=0, 0.8x, M | 12 | 73.44 | 56.130 | 16.203 | 37.8 | 109.1 |
| [15.1-3I]=0, 0.8x CT MM | 12 | 22.74 | 20.036 | 5.784 | 10.0 | 35.5 |
| [15.1-3I]=0, M | 14 | 1359.43 | 173.253 | 46.304 | 1259.4 | 1459.5 |
| [15.1-3I]=0, CT MM | 14 | 326.81 | 113.012 | 30.204 | 261.6 | 392.1 |
| [15.1-3I]=1.75 uM, M | 16 | 1213.21 | 124.120 | 31.030 | 1147.1 | 1279.4 |
| [15.1-3I]=1.75 uM, CT MM | 16 | 43.08 | 25.324 | 6.331 | 29.6 | 56.6 |
| [15.1-3I]=2.2 uM, M | 16 | 1083.57 | 184.631 | 46.158 | 985.2 | 1182.0 |
| [15.1-3I]=2.2 uM, CT MM | 16 | 41.17 | 17.618 | 4.404 | 31.8 | 50.6 |

Effect: Mismatch currents: From 326 nA to 41 nA

Amplicon: *kefyr* 3x buffer AG mismatch

Oneway Analysis of 2 uM By Column 7

Missing Rows 128

Means and Std Deviations

| Level | Number | Mean | Std Dev | Std Err Mean | Lower 95% | Upper 95% |
|---|---|---|---|---|---|---|
| 0 uM | 8 | 1367.93 | 140.237 | 49.58 | 1250.7 | 1485.2 |
| 2 uM | 8 | 1264.75 | 141.040 | 49.87 | 1146.8 | 1382.7 |
| MM2, 0 uM | 8 | 571.18 | 304.228 | 107.56 | 316.8 | 825.5 |
| MM2, 2 uM | 8 | 149.62 | 71.922 | 25.43 | 89.5 | 209.7 |

Effect: Mismatch currents: From ~700 nA to 149 nA

Amplicon: *kefyr* 1.5x buffer AG mismatch

Missing Rows 124

Means and Std Deviations

| Level | Number | Mean | Std Dev | Std Err Mean | Lower 95% | Upper 95% |
|---|---|---|---|---|---|---|
| 0 uM | 8 | 1447.42 | 113.389 | 40.089 | 1352.6 | 1542.2 |
| 2 uM | 10 | 1436.06 | 112.504 | 35.577 | 1355.6 | 1516.5 |
| MM/0 uM | 8 | 302.90 | 199.979 | 70.703 | 135.7 | 470.1 |
| MM/2 uM | 10 | 99.57 | 34.556 | 10.928 | 74.9 | 124.3 |

Effect: Mismatch currents: From >302 nA to 100 nA

INHIBITION OF MISMATCH HYBRIDIZATION BY A UNIVERSAL COMPETITOR DNA

RELATED APPLICATIONS

The present application claims priority to U.S. Provisional Application Ser. No. 60/884,341, filed on Jan. 10, 2007, by Shi, and entitled "INHIBITION OF MISMATCH HYBRIDIZATION BY A UNIVERSAL COMPETITOR DNA," the entire disclosure of which is herein incorporated by reference in its entirety.

SEQUENCE LISTING

The present application is being filed along with a Sequence Listing in electronic format. The Sequence Listing is provided as a file entitled GENOM.074A.TXT, created Dec. 11, 2007, which is 3.99 KB in size. The information in the electronic format of the Sequence Listing is incorporated herein by reference in its entirety.

BACKGROUND OF THE INVENTION

1. Field of the Invention

The present invention generally relates to nucleic acid hybridization methods.

2. Description of the Related Art

Hybridization of polynucleotides to other polynucleotides by Watson-Crick base pairing is a fundamental process useful in a wide variety of research, medical, and industrial applications. Detecting the hybridization of a probe to a polynucleotide containing a target sequence is useful for gene expression analysis, DNA sequencing, and genomic analysis. Particular uses include identification of disease-related polynucleotides in diagnostic assays, screening for novel target polynucleotides in a sample, identification of specific target polynucleotides in mixtures of polynucleotides, identification of variant sequences, genotyping, amplification of specific target polynucleotides, and therapeutic blocking of inappropriately expressed genes, e.g. as described in Sambrook et al., *Molecular Cloning: A Laboratory Manual, 2nd Ed.* (Cold Spring Harbor Laboratory, New York, 1989); Keller and Manak, *DNA Probes, 2nd Ed.* (Stockton Press, New York, 1993); Milligan et al., 1993, *J. Med. Chem.* 36: 1923-1937; Drmanac et al., *Science,* 260: 1649-1652; Bains, 1993, *J. DNA Seq Map,* 4:143-150.

Immobilized probes are useful for detecting polynucleotides containing a target nucleotide sequence, where each immobilized probe is functionally connected to a support and the hybridization of a polynucleotide to the immobilized probe can be detected. Most commonly, DNA probes are used to detect polynucleotides containing a target nucleotide sequence complementary to the probe sequence. The support for immobilized probes may be a flat surface, often called a "chip," or the support may be the surface of a bead or other particle. Probes are usually immobilized in a known arrangement, or array, which provides a medium for matching known and unknown polynucleotides based on nucleic acid hybridization. Microarrays having a large number of immobilized probes of known identity are used to determine complementary binding, allowing massively parallel studies of gene expression and gene discovery. For example, an experiment with a single DNA chip can provide researchers information on thousands of genes simultaneously. For example, Hashimoto et al. disclose an array of immobilized single-stranded probes wherein at least one probe has a nucleotide sequence complementary to the target gene(s) to be detected, such that each probe is immobilized onto the surface of an electrode or the tip of an optical fiber and an electrochemically or optically active substance capable of binding to double-stranded nucleic acids is used to detect hybridization of target genes to complementary immobilized probes (U.S. Pat. Nos. 5,776,672 and 5,972,692).

Nonetheless, probe-based assays have serious limitations that are, at least partially, the result of difficulties associated with specificity, sensitivity and reliability.

At the simplest level, hybridization efficiency between a target nucleic acid and a capture probe is determined by the length of the complementarity between the target and the capture probe, the concentration of the target, and the temperature and the ionic strength of the reaction. It is also influenced by the sequence complexity of the complementary regions, and specifically, by the number of hydrogen bonds which will form between the target and the capture probe. Conventional methods for discriminating a single base pair mismatches in nucleic acid hybridization assays have focused on controlling parameters affecting the stringency of hybridization conditions, such as salt concentration and hybridization temperature. The stability of DNA hybrids in a solution increases as the concentration of cations in the solution increases, due to the ability of the cations to electrostatically shield the anionic phosphate groups in the DNA backbones from each other. Accordingly, hybridization conditions that have higher concentrations of cations, e.g. 5×SSC (0.75M NaCl, 0.075M Sodium Citrate), result in favor the kinetics of hybridization between complementary nucleic acids as well as between mismatched nucleic acids. Because the hybridization kinetics for duplexes is accelerated regardless of DNA sequence, performing the hybridization assays in high salt conditions by itself will not enhance discrimination between hybrids that are fully complementary and those that contain mismatches. On the other hand, allowing the hybridization assays to proceed in low salt conditions (e.g. 0.8×SSC (0.12M NaCl, 0.012 M Sodium Citrate) can enhance the discrimination between fully complementary nucleic acid hybrids and those that contain mismatches. However, the kinetics of hybridization is slowed in conditions of low salt, which in turn adversely affects the sensitivity of the hybridization assay (i.e., the lowest concentration of target DNA which will still yield a positive result). Sequence differences as subtle as a single base (point mutation) in very short oligomers (<10 base pairs "bp") can be sufficient to enable the discrimination of the hybridization to complementary nucleic acid target sequences as compared with non-target sequences. Nonetheless, nucleic acid probes of greater than 10 bp in length are generally required to obtain the sequence diversity necessary to correctly identify a unique organism or clinical condition of interest. However, the ability to discriminate between closely related sequences is inversely proportional to the length of the hybridization probe because the difference in thermal stability decreases between wild type and mutant complexes as the probe length increases. Consequently, the power of probe based hybridization to correctly identify the target sequence of interest from closely related non-target sequences (e.g. targets harboring point mutations) poses several challenges.

In a review entitled "Principles and Practices of Nucleic Acid Hybridization" Kennel et al. teach the use of competitor RNA in a hybridization assay to estimate the specificity of the assay. David E Kennell, Principles and Practices of Nucleic Acid Hybridization, pp. 259-301, hereby expressly incorporated by reference in its entirety. The methods disclosed in Kennel et al. are based on the principle that two identical molecules will compete with each other for a common binding site. Kennel et al. apply this principle to assess similarities between two RNA populations competing for a common DNA. Typically, one population of RNA is labeled and the competitor population of RNA is unlabeled. The competition assay is used to estimate the degree of relation between the two RNA species. A process called "presaturation competition", wherein the unlabeled competitor RNA is hybridized to the DNA before hybridization of the labeled RNA, has been reported to be useful in improving the results of this type of assay. However, the author warns that "great caution should be exercised" in interpreting the data from these assays.

U.S. Pat. No. 5,447,841 to Gray et al. describes methods of in situ hybridization of chromosomal DNA that involve decreasing the ability of labeled nucleic acid fragments to hybridize to repetitive sequences within the chromosomal DNA. Gray et al. disclose blocking the repetitive sequences within the chromosomal DNA by pre-reassociation of fragments with fragments of repetitive-sequence-rich DNA, by pre-reassociation of target DNA with fragments of repetitive-sequence-rich DNA, or pre-reassociation of both the fragments of the heterogeneous mixture and the target DNA with repetitive-sequence-rich DNA. According to Gray et al., this method provides blocking sufficient to permit detection of large labeled nucleic acid (greater than 1000 bp) hybridized to chromosomal DNA.

Methods, kits and compositions that improve the specificity, sensitivity and reliability of probe-based assays would be useful in the detection, analysis and quantitation of nucleic acid containing samples. There exists a need for an alternative to controlling the stringency of hybridization, e.g. with low salt or high temperature, to enable the discrimination of single base pair mismatches in nucleic acid hybridization assays, which maintaining sufficient detection sensitivity at low concentrations of amplicons.

SUMMARY

In a first aspect, provided herein are methods for increasing hybridization efficiency between a capture probe and a target nucleic acid. In some embodiments, a probe complex including both a capture probe and a linker sequence is provided. The capture probe can include a nucleic acid that is complementary to a target nucleic acid sequence. The linker sequence can be linked to the capture probe. A competitor nucleic acid and a target nucleic acid can also be provided. The competitor nucleic acid can include a complementary region that is fully complementary or substantially complementary to the linker sequence and a universal region that includes at least about two universal bases that can hybridize to more than one nucleotide selected from A, T, C, and G. The universal region can be linked to the 5' end of the complementary region of the competitor nucleic acid. The probe complex can be contacted with the target nucleic acid and said competitor nucleic acid.

In some embodiments, the universal region of the competitor nucleic acid includes at least about 2, 3, 4, 5, or 6 universal bases that can hybridize to more than one nucleotide selected from A, T, C, and G. Preferably, the universal region comprises, consists essentially of, or consists of about 3 universal bases.

In some embodiments, the universal base can be selected from the group consisting of deoxyinosine, 3-nitropyrrole, 4-nitroindole, 6-nitroindole, 5-nitroindole. Preferably, the universal base is deoxyinosine.

In some embodiments, the linker sequence of the probe complex is about 7 to about 45 nucleotides in length, and preferably is about 10 to about 20 nucleotides in length. In some embodiments, the capture probe of the probe complex is about 7 to about 45 nucleotides in length and is preferably about 10 to about 20 nucleotides in length. In some embodiments, the linker sequence and the capture probe of the probe complex are about the same length. In other embodiments, the linker sequence is longer than the length of the capture probe of the probe complex, and in yet other embodiments, the linker sequence is shorter than the length of the capture probe of the probe complex.

In some embodiments, the competitor nucleic acid can anneal to the linker sequence under conditions of high salt, for example 5×SSC at about 50-60° C.

In some embodiments disclosed herein, the competitor nucleic acid is provided at a final concentration of about 0.1 μM to about 5 mM. In some embodiments, the competitor nucleic acid is provided at a final concentration of about 1.5 μM to about 3.5 mM, or at a concentration of about 1.3 mM to about 2.2 mM. In some embodiments, the competitor nucleic acid can be provided in a molar excess relative to the amount of target sequence, at approximately the same concentration compared to the target sequence, or at a lower concentration compared to the target sequence. For example, in some embodiments, the concentration of competitor nucleic acid is about 30 times to about 135 times higher than the concentration of the target nucleic acid or amplicon.

Non-limiting examples of different assay conditions useful in the methods described herein are shown in Table 1, below:

TABLE 1

| Target/ Competitor Relationship | Concentration of Target Nucleic Acid | Concentration of Competitor Nucleic Acid | Target: Competitor Ratio | Salt Concentration |
|---|---|---|---|---|
| TG mismatch | 25 nM | 1000 nM | 40 | 5xSSC |
| CT mismatch | 35 nM | 1750 nM | 50 | 3xSSC |
| AC mismatch | 25 nM | 2000 nM | 80 | 3xSSC |
| AG mismatch | 25 nM | 2000 nM | 133 | 1.5xSSC |

In a second aspect, provided herein are compositions to increase hybridization efficiency between a capture probe of a probe complex and a target nucleic acid, including a competitor nucleic acid. The probe complex can include a capture probe nucleic acid sequence that can be complementary to a target nucleic acid sequence, and which can be linked to a linker sequence. The competitor nucleic acid can include a complementary region that can be fully complementary or substantially complementary to the linker sequence. The competitor nucleic acid can also include a universal region. The universal region of the competitor nucleic acid can include at least about two universal bases that can hybridize to more than one, and preferably all nucleotides selected from A, T, C, and G. The universal region can be adjacent to the 5' end of the complementary region of the competitor nucleic acid.

In some embodiments, the universal region can include at least about 2, 3, 4, 5, or 6 universal bases that can hybridize to more than one nucleotide selected from A, T, C, and G. Preferably, the universal region comprises, consists essentially of, or consists of about 3 universal bases that can hybridize to A, T, C, or G.

In some embodiments, the universal base(s) can be selected from the group consisting of deoxyinosine, 3-ntiropyrorole, 4-nitroindole, 6-nitroindole, 5-nitroindole. Preferably, the universal base is deoxyinosine, or any combination thereof.

In some embodiments, the complementary region of the competitor nucleic acid is about 7 to about 45 nucleotides in length, and is fully complementary to about 7 to 45 consecutive nucleotides of the linker sequence. For example, in some embodiments, the complementary region of the competitor nucleic acid is about 10 to about 20 nucleotides in length and is fully complementary or substantially complementary to the linker sequence of the probe complex.

In some embodiments, the competitor nucleic acid can anneal to the linker sequence under conditions of high salt, such as, for example 5×SSC at about 50-60° C.

In some embodiments, the ratio of the melting temperature ($T_m$) of the capture probe and the competitor nucleic acid is approximately one, i.e., the $T_m$'s are approximately the same. In other embodiments, the $T_m$ of the competitor nucleic acid is higher than the $T_m$ of the capture probe.

In preferred embodiments, the probe complex is attached to a solid support. Preferably, the linker sequence of the probe complex is operably attached to a solid support.

Other aspects relate to competitor nucleic acids to increase hybridization efficiency between a probe complex and a target nucleic acid. The probe complex can include a complementary region that is fully complementary or substantially complementary to a target nucleic acid sequence. The probe complex can also include a linker sequence that is linked to the capture probe sequence.

The competitor nucleic acid can include a complementary region that is fully complementary or substantially complementary to the linker sequence, and a universal region comprising at least about two universal bases, with the universal region liked to the 5' end of the complementary region of the competitor nucleic acid.

The universal region can comprise, consist essentially of, or consist of at least about 2, 3, 4, 5, or 6 universal bases, and preferably includes about 3 universal bases. Preferably, the universal bases can hybridize to any naturally occurring nucleotide. In some embodiments, the universal base is selected from the group consisting of deoxyinosine, 3-ntiropyrorole, 4-nitroindole, 6-nitroindole, and 5-nitroindole, or any combination thereof. In some embodiments, the universal base(s) is/are deoxyinosine. In some embodiments, the universal region comprises more than one type of universal base.

In some embodiments, the complementary region of the competitor nucleic acid can be about 7 to about 45 nucleotides in length, preferably about 10 to about 20 nucleotides in length. In preferred embodiments, the complementary region is about the same length as the linker region of the probe complex.

DETAILED DESCRIPTION

Figure 1:
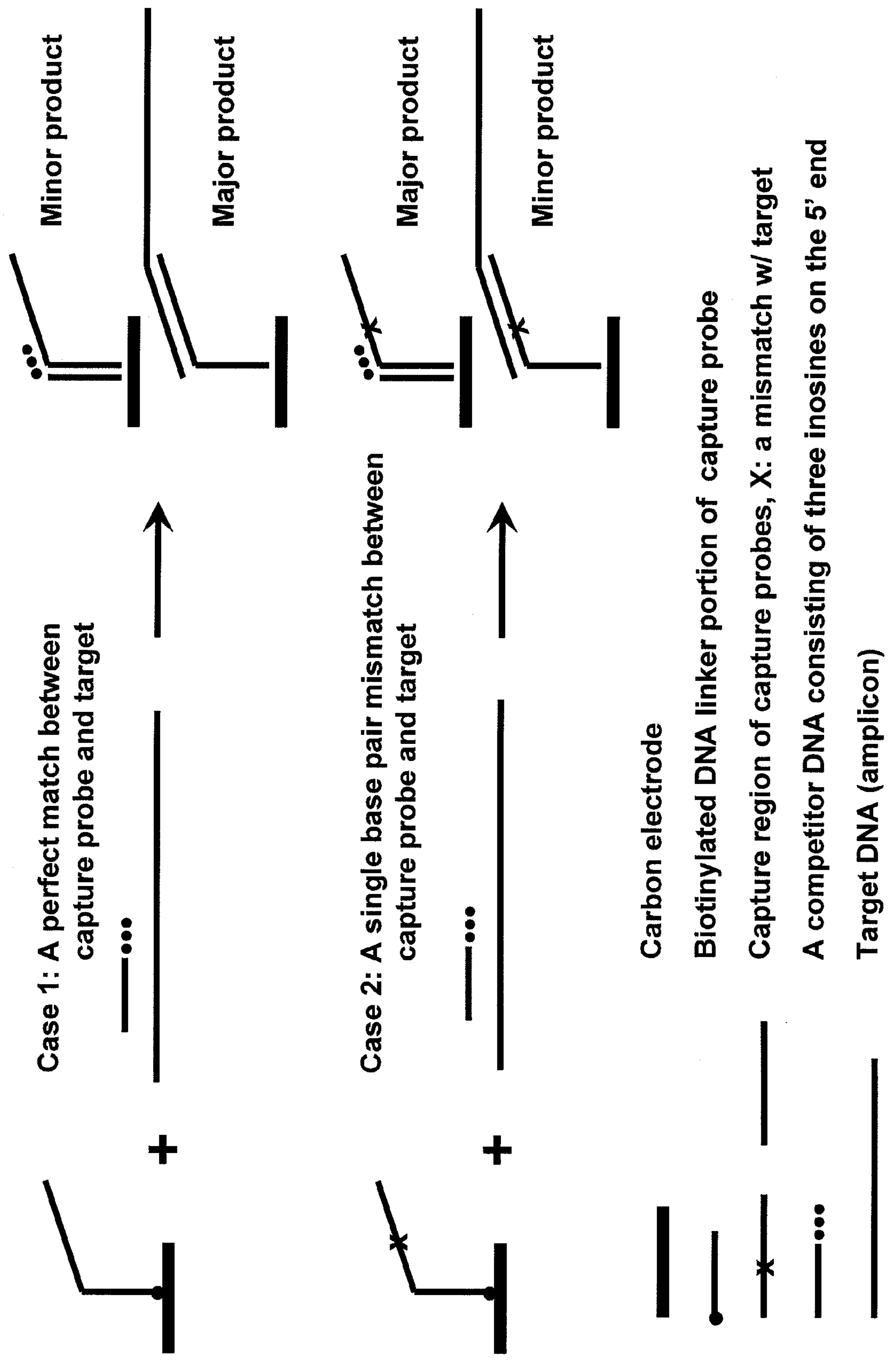
FIG. 1 is a graphical representation of an example of the capture probe technology described herein. In case 1, the capture probe and target sequences are fully complementary. In the presence of both the target and the competitor nucleic acid, the major hybridization product is the capture probe/target. In case 2, the capture probe and the target sequences are not fully complementary. In this case, in the presence of both the target and the competitor nucleic acid, the major hybridization product is the competitor DNA/capture probe.

The present invention generally relates to methods and compositions for improving nucleic acid hybridization assays to detect target nucleic acids in a sample. The methods and compositions described herein can decrease the hybridization efficiency of non-target sequences compared to target sequences to capture probes that are complementary to a target sequence, thereby increasing the sensitivity and specificity of the hybridization assay.

Nucleic Acid Hybridization Assays

The term "nucleic acid hybridization assays" generally refers to assays in which single-stranded analyte nucleic acids, e.g., target nucleic acids, are hybridized to single stranded nucleic acid probes. The duplex formed between complementary nucleic acids is detected by various means known to those skilled in the art, e.g. via a signal. A signal refers to any detectable (i.e., identifiable) indicator of the presence or occurrence of an event of interest, e.g., a binding event between two complementary nucleic acids. Signals that are detected in the present invention may vary depending on the signal producing system employed, where the signals may be isotopic, fluorescent, electrical, etc. In preferred embodiments, the duplex is detected electrochemically, as described, for example in co-pending U.S. patent application Ser. No. 10/429,293, the disclosure of which is herein incorporated by reference in its entirety.

In some embodiments, the signal is generated by a label. Labels of interest include directly detectable and indirectly detectable radioactive or non-radioactive labels such as fluorescent dyes. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of indirectly detectable labels include biotin or digoxigenin, which can be detected by a suitable antibody coupled to a fluorochrome or enzyme, such as alkaline phosphatase. In many preferred embodiments, the label is a directly detectable label. Directly detectable labels of particular interest include fluorescent labels. Fluorescent labels that find use in the subject invention include a fluorophore moiety. Specific fluorescent dyes of interest include: xanthene dyes, e.g., fluorescein and rhodamine dyes, such as fluorescein isothiocyanate (FITC), 2-[ethylamino)-3-(ethylimino)-2-7-dimethyl-3H-xanthen-9-yl]benzoic acid ethyl ester monohydrochloride (R6G) (emits a response radiation in the wavelength that ranges from about 500 to 560 nm), 1,1,3,3,3',3'-Hexamethylindodicarbocyanine iodide (HIDC) (emits a response radiation in the wavelength that ranged from about 600 to 660 nm), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g. Cy3, Cy5 and Cy7 dyes; coumarins, e.g., umbelliferone; benzimide dyes, e.g. Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3 (emits a response radiation in the wavelength that ranges from about 540 to 580 nm), Cy5 (emits a response radiation in the wavelength that ranges from about 640 to 680 nm), etc; BODIPY dyes and quinoline dyes. Specific fluorophores of interest include: Pyrene, Coumarin, Diethylaminocoumarin, FAM, Fluorescein Chlorotriazinyl, Fluorescein, R110, Eosin, JOE, R6G, HIDC, Tetramethylrhodamine, TAMRA, Lissamine, ROX, Napthofluorescein, Texas Red, Napthofluorescein, Cy3, and Cy5, and the like.

Nucleic acid hybridization assay procedures and conditions are known to those skilled in the art and are described, for example, in Maniatis et al. "Molecular Cloning: A Laboratory Manual," 2nd Ed. Cold Spring Harbor Press, N.Y., (1989), Berger and Kimmel, Methods in Enzymology, Vol. 152, "Guide to Molecular Cloning Techniques", Academic Press, Inc., San Diego, Calif. (1987); Young and Davis, Proc. Nat. Acad. Sci. USA, Vol. 80: 1194 (1983).

As used herein, when referring to nucleic acid hybridization assays, the term sensitivity refers to the lowest concentration of target DNA that is detectable in the assay. An increase in the sensitivity of the nucleic acid hybridization assays therefore refers to a situation in which the concentration on target DNA detectable in an assay is decreased compared to the reference assay.

The term specificity refers to how well the assay detects a specific target, and does not detect closely-related sequences, e.g. non-target nucleic acids containing one mismatch. An increase in specificity thus refers to an enhanced ability to distinguish between closely related target and non-target sequences under specified assay conditions.

The term "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positively-charged backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp. 69-176). Several nucleic acid analogs are described in Rawls, C & E News Jun. 2, 1997 p. 35. All of these references are hereby expressly incorporated by reference. Modifications of the ribose-phosphate backbone may be done to facilitate the addition of labels, or to increase the stability and half-life of such molecules in physiological environments, for example. The term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside.

As discussed above, the methods and compositions described herein can decrease the hybridization efficiency of non-target sequences compared to target sequences to capture probes. “Hybridizing”, “annealing” and “binding”, with respect to polynucleotides, are used interchangeably. “Binding efficiency” refers to the productivity of a binding reaction, measured as either the absolute or relative yield of binding product formed under a given set of conditions in a given amount of time. “Hybridization efficiency” is a particular sub-class of binding efficiency, and refers to binding efficiency in the case where the binding components are polynucleotides.

Probe Complexes

In some embodiments, a probe complex is provided, comprising a capture probe and a linker sequence. The capture probe of the probe complex can be linked to the linker sequence. Preferably, the capture probe is linked to the 5' end of the linker sequence.

When two sequences are “linked,” they are joined either by a typical phosphodiester bond, or are linked via any other means known to those skilled in the art. In preferred embodiments, sequences are linked via a typical phosphodiester bond. In other embodiments, the linkage between the nucleotides of two sequences (e.g., the universal and complementary regions of competitor nucleic acids, or the capture probe and linker regions of probe complexes), can include, but are not limited to: (i) substitution of oxygen in the internucleotide linkage by sulfur, carbon, or nitrogen, and (ii) sulfate, carboxylate, and amide internucleotide phosphodiester linkages. Other preferred internucleotide analogs include; 2-aminoethylglycine (PNA), 2'-5'-linkage, inverted 3'-3' linkage, inverted 5'-5' linkage, phosphorothioate, phosphorodithioate, methyl phosphonate, non-bridging N-substituted phosphoramidate, alkylated phosphotriester branched structure, and 3'-N-phosphoramidate.

Capture probes can contain a complementary region that is fully complementary or substantially complementary to a target nucleic acid sequence.

The complementary region of the capture probe is substantially complementary to the target nucleic acid. DNA typically contains a polynucleotide composed of the 4 “natural” bases: A (adenine), T (thymine), C (cytosine), and G (guanine). The hydrogen bonding (or base pairing) among these nucleotides creates the double-stranded structure of a DNA molecule. An A-containing residue base pairs to a T-containing residue through the formation of two hydrogen bonds; a G-containing residue base pairs to a C-containing residue through the formation of three hydrogen bonds. This base-paring is commonly known as Watson-Crick base-paring. Double-stranded DNA denatures at high temperature into single strands and then renatures when the temperature is lowered below the “melting” temperature ($T_m$) of the DNA strands. The same principle applies to other nucleic acid such as RNA.

As used herein, the term “substantially complementary” refers to the complementarity between two nucleic acids, e.g. the complementary region of the capture probe and the target sequence, and/or between the linker sequence of the capture probe and the complementary region of the competitor nucleic acid. The complementarity need not be perfect; there may be any number of base pair mismatches that between the two nucleic acids. However, if the number of mutations is so great that no hybridization can occur under even the least stringent of hybridization conditions, the sequence is not a substantially complementary sequence. When two sequences are referred to as “substantially complementary” herein, it is meant that the sequences are sufficiently complementary to the each other to hybridize under the selected reaction conditions. The relationship of nucleic acid complementarity and stringency of hybridization sufficient to achieve specificity is well known in the art and described further below in reference to sequence identity, melting temperature and hybridization conditions. Therefore, substantially complementary sequences can be used in any of the detection methods of the invention. Such probes can be, for example, perfectly complementary or can contain from 1 to many mismatches so long as the hybridization conditions are sufficient to allow, for example discrimination between a target sequence and a non-target sequence. Accordingly, substantially complementary sequences can refer to sequences ranging in percent identity from 100, 99, 98, 97, 96, 95, 94, 93, 92, 91, 90, 89, 85, 80, 75 or less, or any number in between, compared to the reference sequence.

In embodiments described herein, the capture probe comprises a complementary region that is substantially complementary to the target sequence, and a linker sequence that is substantially complementary to a complementary region on the competitor nucleic acid.

The linker sequence can be any nucleic acid sequence that is not naturally co-extensive with or that does not naturally occur linked to the sequence of the complementary region. The linker sequence can be artificial, i.e., non-naturally occurring, or it can be derived from the same source (organism) as the target sequence, so long as it is not naturally co-extensive with or linked to the complementary region sequence. Alternatively, the linker sequence can be derived from a heterologous source.

In some embodiments, the probe complex is functionally linked to a solid support. Preferably, the linker region of the probe complex is linked to a solid support. In some embodiments, the probe complex is operably attached or stably associated with a solid support. The support may be a flexible or rigid support. By “stably associated” it is meant that the probe complex maintains its position relative to the solid support under hybridization and washing conditions. As such, the probe complexes can be non-covalently or covalently stably associated with the support surface based on technologies well known to those of skill in the art. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the spot oligonucleotides and a functional group present on the surface of the rigid support, e.g. —OH, where the functional group may be naturally occurring or present as a member of an introduced linking group. In many preferred embodiments, the probe complexes are covalently bound to the support surface, e.g. through covalent linkages formed between moieties present on the probe complexes (e.g. thymine bases) and the substrate surface, etc.

As mentioned above, the probes can be associated with or functionally linked to either a flexible or rigid substrate. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible.

As such, the rigid substrates of the subject arrays are sufficient to provide physical support and structure to the polymeric targets present thereon under the assay conditions in which the array is employed. Furthermore, when the rigid supports of the subject invention are bent, they are prone to breakage. The skilled artisan will appreciate that probe complexes can be arranged on the solid supports in a variety of configurations.

The solid supports disclosed herein may be fabricated by conventional means known to those skilled in the art, such as, for example, the methods disclosed in U.S. patent application Ser. No. 10/914,114, filed Aug. 9, 2004, and references cited therein, the disclosures of which are hereby expressly incorporated by reference in their entirety.

Preferably, the probe complexes are linked to a substrate that enables electrochemical detection of nucleic acids. Methods for attaching nucleic acids, e.g. probe complexes to an electrical contact surface are well known, for example as disclosed in any of U.S. Pat. Nos. 5,312,527, 5,776,672, 5,972,692, 6,200,761, and 6,221,586, the disclosures of which are incorporated herein by reference in their entireties.

Electrochemical detection of nucleic acids is known to those skilled in the art and is described, for example, in U.S. patent application Ser. No. 10/429,293, filed May 2, 2003, and U.S. patent application Ser. No. 10/429,291, filed May 2, 2003, and references cited therein, the disclosures of which are hereby incorporated by reference in their entireties.

Target Sequences

Target nucleic acid segments or analyte nucleic acids to be analyzed in nucleic acid hybridization assays described herein may be DNA, cDNA, RNA, including mRNA and rRNA or others. The target nucleic acid may be double stranded or single stranded. As described in more detail in Mullis, et al., U.S. Pat. No. 4,683,195 and Mullis, U.S. Pat. No. 4,683,202, any source of nucleic acid, in purified or nonpurified form, can be utilized as the starting nucleic acid or acids, if it contains, or is suspected of containing, the target nucleic acid. The target nucleic acid can be only a fraction of a larger molecule or can be present initially as a discrete molecule. Additionally, the target nucleic acid may constitute the entire nucleic acid or may be a fraction of a complex mixture of nucleic acids. For example, the target sequence may be a portion of a gene, a regulatory sequence, genomic DNA, cDNA, RNA including mRNA and rRNA, or others. The target nucleic acid may be any length, with the understanding that longer sequences are more specific. The size of the target nucleic acid and the linker sequence may vary, as will be appreciated by those in the art with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the complementary regions of the capture probes are each preferably about 15-20 nucleotides in length, e.g. about 18 nucleotides in length.

As is outlined herein, the target sequence may be a target sequence from a sample, or a secondary target such as a product of a reaction such as a detection sequence from an invasive cleavage reaction, a ligated probe from an oligonucleotide ligation assay reaction ("OLA"), an extended probe from a PCR reaction, or PCR amplification product, ("amplicon") etc. As will be appreciated by those in the art, the complementary target sequence may take many forms. For example, it may be contained within a larger nucleic acid sequence, i.e., all or part of a gene or mRNA, a restriction fragment of a plasmid or genomic DNA, among others. The capture probes, particularly the complementary regions, are designed to hybridize to target sequences to determine the presence or absence of the target sequence in a sample.

Competitor Nucleic Acids

In some embodiments, a competitor nucleic acid is provided. Competitor nucleic acids can include a complementary region that is fully complementary or substantially complementary to the linker sequence of the probe complex. Preferably, the complementary region is fully complementary to the linker sequence of the probe complex.

The 5' end of the complementary region can be linked to a universal region. Universal regions can include 2, 3, 4, 5, 6 or more universal bases. The term "universal base" is intended to refer to nucleotide analogs that form fewer hydrogen bonds with naturally occurring nucleotides, i.e., adenosine, guanine, thymine, and cytosine, than between naturally occurring nucleotides. Universal bases can be hydrophobic base analogs that lack hydrogen bonding groups, yet which can pack efficiently in duplex DNA can show little selectivity in pairing with natural bases. Millican, T. A., et al. (1984) *Nuc. Acids Res.* 12:7435-7453; Schweitzer, B. A., et al. (1995) *J. Am. Chem. Soc.* 117:1863-1872; Matray, T. J., et al. (1999) *Nature* 399: 704-708; Ogawa, A. K., et al. (2000) *J. Am. Chem. Soc.* 122:3274-3287, the disclosures of which are hereby expressly incorporated by reference in their entireties. Nucleobase analogs that can hybridize non-selectively to each of the native bases have been described. Van Aerschot, A., et al. (1995) *Nucl. Acids Res.* 23: 4363-4370; Zhang, P. et al. (1998) *Nucl. Acids Res.* 26: 2208-2215; Seela, F. et al. (1999), *Nucleosides Nucletodies* 18:425-441; Bergstrom, D. E., et al. (1997) *Nucl. Acids Res.* 25: 1935-1942; Asomova, O., et al. (1997) *Nucl. Acids Res.* 25: 1930-1934; Bergstrom, D. E., et al., (1995) *J. Am. Chem. Soc.* 117: 1201-1209; Loakes, D. et al. (1995) *Nucl. Acids Res.* 23: 2361-2366; Loakes, D. et al. (1995) *Nucl. Acids Res.* 22: 4039-4043; Nichols, R., et al., (1994) *Nature* 369: 492-493. As will be appreciated by those in the art, all known nucleic acid analogs may find use in the present invention. Non-limiting examples of universal bases useful in the methods and compositions described herein include: deoxyinosine, dexoyribionucleotides of 3-nitropyrrole (1,2), or 4-, 5-, or 6-nitro-indole, 1-(2'-deoxy-β-D ribofuranosyl)-4-nitropyrazole, and 1-(2'-deoxy-β-D ribofuranosyl)-4-nitroimidazole.

In some embodiments, the nucleic acids are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C., therefore allowing for better detection of mismatches. Similarly, due to their non-ionic nature, hybridization of the bases attached to these backbones is relatively insensitive to salt concentration.

Deoxyinosine ("dI") is a preferred example of a universal base. Inosine is capable of forming two hydrogen bonds with either A, C, T, or G (See, Barker, R., Organic Chemistry of Biological Molecules, Prentice-Hall, N.J. (1971); See also, Martin et al. (1985), Nucl. Acids Res. 13(24): 8927-8938). Other preferred examples of universal bases include 1-(2'- deoxy-β-D ribofuranosyl)-3-nitropyrrole, 1-(2'-deoxy-β-D ribofuranosyl)-4-nitropyrazole, 1-(2'-deoxy-β-D ribofuranosyl)-4-nitroimidazole, and 1-(2'-deoxy-β-D ribofuranosyl)-4-nitroindole.

In some embodiments, the target nucleic acid is contacted with the probe complex and the competitor nucleic acid. In some embodiments, the target nucleic acid is contacted first with the competitor nucleic acid, and then the probe complex. In other embodiments, the target nucleic acid is contacted with the competitor nucleic acid and the probe complex substantially simultaneously, i.e., at the same time, within 1 second, within 2 seconds, within 5 seconds, within 20 seconds, within 30 seconds, within 1 minute, within 1.5 minutes, within 2 minutes, within 5 minutes, within 10 minutes, within 15 minutes, within 20 minutes, within 30 minutes, within 45 minutes, within 1 hour, or more. In some embodiments, the target nucleic acid is contacted with the probe first, and then the competitor nucleic acid.

Compositions

Also provided herein are compositions that comprise, consist of, or consist essentially of a competitor nucleic acid, such as those described above. The competitor nucleic acid can increase the hybridization efficiency between a probe complex and a target nucleic acid, and/or decrease the hybridization efficiency between a probe complex and a non-target nucleic acid, wherein the probe complex includes a complementary region with a nucleic acid that is complementary to the target nucleic acid sequence. The probe complex can also include a linker sequence, wherein the capture probe and said linker sequence are linked.

Competitor nucleic acids described herein can include a complementary region that is substantially complementary to the linker sequence, and a universal region comprising at least about two universal bases, wherein the universal region is adjacent to the 5' end of said complementary region of said competitor nucleic acid.

Preferably, the universal region of the competitor nucleic acid can include at least about 2, 3, 4, 5, or 6 universal bases. Most preferably, the competitor nucleic acid the universal region includes 3 universal bases. In preferred embodiments, the universal base(s) is selected from the group consisting of deoxyinosine, 3-ntiropyrorole, 4-nitroindole, 6-nitroindole, and 5-nitroindole. Each of the universal bases of the competitor nucleic acid can be the same or different.

Having generally described this invention, a further understanding can be obtained by reference to certain specific examples which are provided herein for purposes of illustration only, and are not intended to be limiting.

EXAMPLES

Example 1

Linker Sequence does not Affect Hybridization of Target Nucleic Acids to Capture Probes To determine if the particular nucleotide sequence of the linker of a probe complex influences the ability to electrochemically detect the hybridization of a target DNA sequence to a capture probe, hybridization experiments with probe complexes with two different linker sequences and identical capture probe sequences were performed.

Briefly, a probe complex containing either the 10A linker (SEQ ID NO: 1) or a C1 linker (SEQ ID NO: 2) attached to a biotin complex is bound to a carbon electrode containing a porous layer of avidin on its surface, thereby immobilizing the probe complexes on the electrode surface. The capture probe portion of the probe complex contains the following sequence derived from *Candida glabrata* (SEQ ID NO: 3).

A 294 bp amplicon of SEQ ID NO: 4 of *C. glabrata* was prepared in 3×SSC/0.05% Tween 20 in 2 µM anti-DIG-POD solution (Boerhinger Mannheim). 25 µl of the mixture transferred to a solid support for 20 minutes at 58-59° C. in a VWR oven. The chips were removed and 300 µl of 1×SSC was applied to dilute the solution on the chip surface. Chips were allowed to cool at room temperature for 2 minutes. The chips were then seabed with Ahlstrom filter paper, grade 320. 80 µl of K-Blue substrate (Neogen, Mich.) containing additional 4.5 mM $H_2O_2$ was added to the chip.

For detection, the chip is washed three times with a ruthenium detection solution containing 5 µM $Ru(NH_3)_6^{3+}$, 10 mM Tris and 10 mM NaCl at pH 7.4. Binding of ruthenium to hybridized nucleic acids is measured using amperometry.

Figure 2:
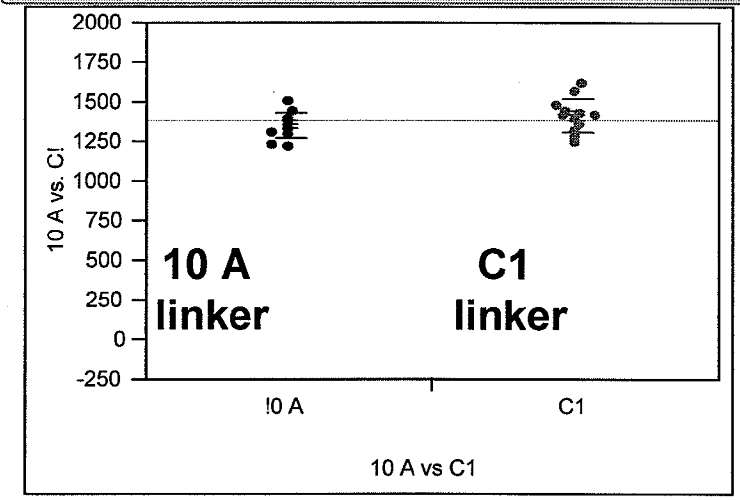
FIG. 2 is a graph of electrochemical measurements reflecting the amount of target sequence (DNA derived from *Candida glabrata*) hybridized to two different probe complexes. The probe complexes contain identical capture probe regions, but different linker sequences, i.e., 10A or C1.

The results are presented in FIG. 2 and Table 2. No difference in specificity or sensitivity limits were seen between the different probe complexes tested, indicating that the linker sequence of the probe complex does not affect the detection of target sequences.

TABLE 2

Means and Standard Deviations

| Level | Number | Mean | Std. Dev. | Std. Err. Mean | Lower 95% | Upper 95% |
|---|---|---|---|---|---|---|
| 10A | 12 | 1352.48 | 83.232 | 24.027 | 1299.6 | 1405.4 |
| C1 | 12 | 1413.94 | 109.291 | 31.550 | 1344.5 | 1483.4 |

Example 2

Competitor Nucleic Acids Enhance Distinction Between Fully Complementary Target/Capture Probe Hybrids and Mismatched Target/Capture Probe Hybrids To assess the ability of competitor nucleic acids to enhance the discrimination between fully complementary (matched) target/capture probe complexes and mismatched target/capture probe hybrids, the amperometric readings of hybridization reactions between capture probes containing *C. gulliermondii* or *C. tropicalis* sequences (SEQ ID NOs: 5 and 6 respectively) and *C. gulliermondii* target DNA (SEQ ID NO: 7) were measured and compared. The *C. tropicalis* (MM) capture probe contains a T:G mismatch with respect to the *C. gulliermondii* target DNA, located at the 3' end of the capture probe sequence. The *C. gulliermondii* capture probe (M) is fully complementary to the *C. gulliermondii* target DNA.

The probe complexes are attached to an electrode surface as described in Example 1. A 266 bp amplicon (SEQ ID NO: 7) of *C. gulliermondii* target DNA was allowed to hybridize to the probe complex as described in Example 1 in (1) 0.8×SSC; (2) 5×SSC; or (3) 5×SSC in the presence of 1.3 µM of a competitor DNA probe [15.1-31] (SEQ ID NO: 8). The detection steps were carried out as described in Example 1.

Figure 3:
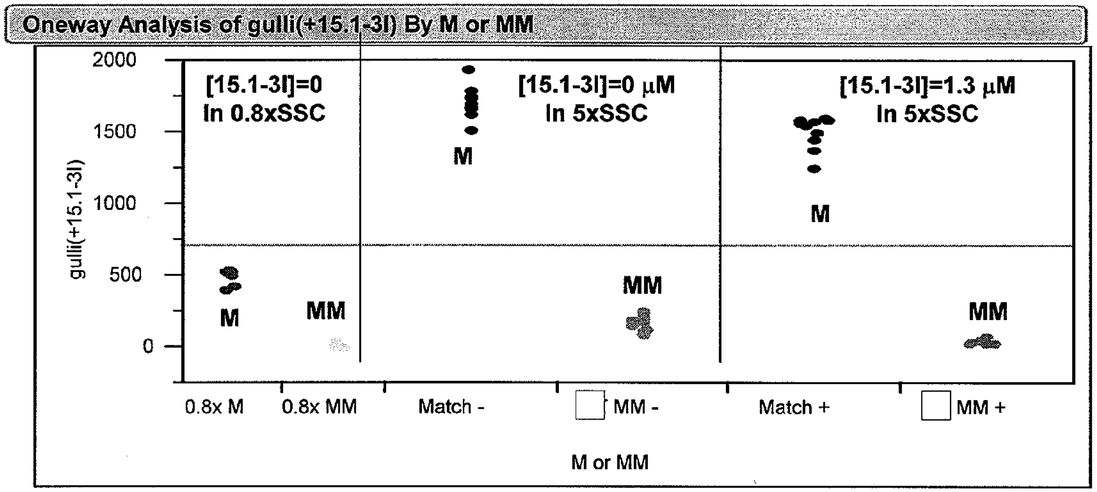
FIG. 3 is a graph of electrochemical measurements reflecting the amount of target sequence (DNA derived from *Candida gulliermondii*) hybridized to two different probe complexes, M and MM. As indicated, the hybridization reactions were carried out with or without competitor nucleic acids in either 0.8×SSC or 5×SSC. The two probe complexes in the assay contain identical linker sequences (SEQ NO. 2), but contain capture probe regions that are either fully complementary (M) to the target DNA or have a T:G mismatch (MM) relative to the target DNA. The mismatch is in the MM capture probe located 2 nucleotides from the end of the probe.

The results are presented in FIG. 3 and Table 3. The addition of competitor DNA to high salt hybridization conditions in the electrochemical hybridization assay generated a lower signal than when the assay was conducted in the absence of competitor DNA, e.g. 33nA compared to 152nA. These results demonstrate that the presence of competitor nucleic acids in the hybridization assays allows for increased assay sensitivity at higher salt concentrations.

TABLE 3

| Level | Number | Mean | Std. Dev. | Std. Err. Mean | Lower 95% | Upper 95% |
|---|---|---|---|---|---|---|
| 0.8xSSC (M) | 6 | 480.68 | 57.210 | 23.356 | 421 | 540.7 |
| 0.8xSSC (MM) | 6 | 12.77 | 12.781 | 5.218 | −0.6446 | 26.2 |
| 5xSSC (M) no competitor | 10 | 1706.06 | 108.189 | 34.212 | 1629 | 1783.5 |
| 5xSSC (MM) no competitor | 10 | 152.57 | 51.543 | 16.299 | 116 | 189.4 |
| 5xSSC (M) 1.3 µM competitor | 10 | 1499.32 | 114.390 | 36.173 | 1417 | 1581.1 |
| 5xSSC (MM) 1.3 µM competitor | 10 | 33.27 | 16.429 | 5.195 | 22 | 45.0 |

Example 3

Competitor Nucleic Acids Enhance Distinction Between Fully Complementary Target/Capture Probe Hybrids and Mismatched Target/Capture Probe Hybrids To assess whether the sequence of the mismatch affects the ability of competitor DNA probes to discriminate target from mismatch DNA, the amperometric readings of hybridization reactions between capture probes containing *C. gulliermondii* or *C. tropicalis* sequences, (SEQ ID NOs: 5 and 6 respectively) and *C. tropicalis* target DNA (SEQ ID NO: 9) were measured and compared. The *C. gulliermondii* (MM) capture probe contains a A:C mismatch with respect to the *C. tropicalis* target DNA, located at the 3' end of the capture probe sequence. The *C. tropicalis* capture probe (M) is fully complementary to the *C. tropicalis* target DNA.

The probe complexes are attached to an electrode surface as described in Example 1. A 263 bp amplicon (SEQ ID NO: 9) of *C. tropicalis* target DNA was allowed to hybridize to the probe complex as described in Example 1 in (1) 0.8xSSC; (2) 5xSSC; or (3) 5xSSC in the presence of 2.0 µM of a competitor DNA probe [15.1-31] (SEQ ID NO: 8). The washing, rinsing, and detection steps were carried out as described in Example 1.

Figure 4:
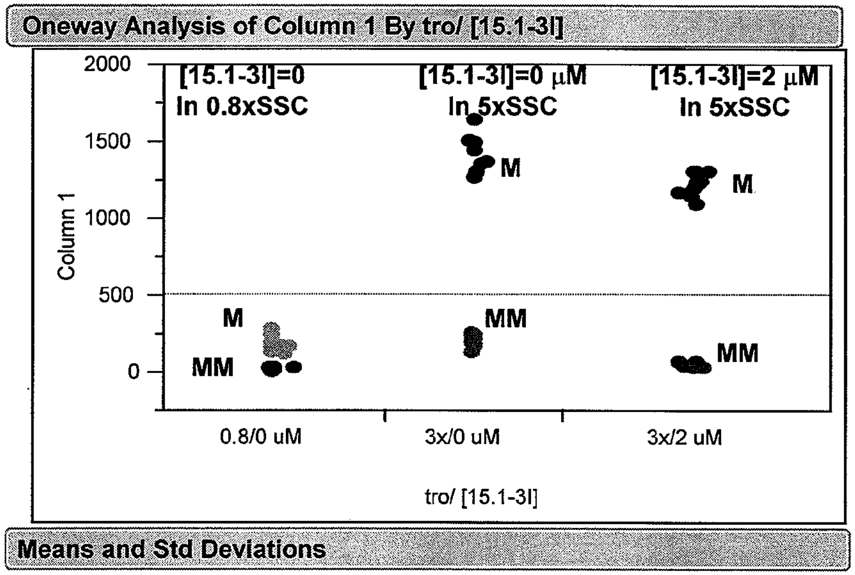
FIG. 4 is a graph of electrochemical measurements reflecting the amount of target sequence (DNA derived from *Candida tropicalis*) hybridized to two different probe complexes, M and MM. As indicated, the hybridization reactions were carried out with or without competitor nucleic acids in either 0.8×SSC or 3×SSC. The two probe complexes assayed contain identical linker sequences (SEQ NO. 2), but have capture probe regions that are either fully complementary (M) to the target DNA or have an A:C mismatch (MM) resulting in a one base-pair mismatch with the target DNA. The mismatch in the MM probe is located 2 nucleotides from the end of the probe.

The results are presented in FIG. 4 and Table 4. The addition of competitor DNA to high salt hybridization conditions in the electrochemical hybridization assay generated a lower signal than when the assay was conducted in the absence of competitor DNA, e.g. 48nA compared to 202nA. In reactions with mismatch amplicons (MM), and competitor nucleic acids, the signal decreases. The signal also decreases when competitor nucleic acid is added to a reaction with a match (M) amplicon, however, the decrease in signal seen with the MM amplicon is much less compared to the decrease seen with the match amplicon. As such, distinguishing between a match and a mismatch is much easier to detect due to the differential effect of the presence of competitor nucleic acids on the signal.

TABLE 4

| Level | Number | Mean | Std. Dev. | Std. Err. Mean | Lower 95% | Upper 95% |
|---|---|---|---|---|---|---|
| 0.8xSSC (M) | 10 | 183.57 | 48.246 | 15.257 | 149.1 | 218.1 |
| 0.8xSSC (MM) | 10 | 25.18 | 9.461 | 2.992 | 18.4 | 31.9 |
| 5xSSC (M) no competitor | 8 | 1423.16 | 123.563 | 43.686 | 1319.9 | 1526.5 |
| 5xSSC (MM) no competitor | 8 | 202.94 | 41.925 | 14.823 | 167.9 | 238.0 |
| 5xSSC (M) 2.0 µM competitor | 12 | 1230.40 | 71.345 | 20.595 | 1185.1 | 1275.7 |
| 5xSSC (MM) 2.0 µM competitor | 12 | 48.35 | 11.635 | 3.359 | 41.0 | 55.7 |

Example 4

Competitor Nucleic Acids Enhance Distinction Between Fully Complementary Target/Capture Probe Hybrids and Mismatched Target/Capture Probe Hybrids To assess whether the location of the mismatch or the concentration of competitor affects the ability of competitor DNA probes to discriminate target from mismatch DNA, the amperometric readings of hybridization reactions between capture probes containing *C. glabrata* or *C. kefyr* sequences, (SEQ ID NOs: 10 and 11 respectively) and *C. glabrata* target DNA (SEQ ID NO: 12) were measured and compared. The *C. kefyr* (MM) capture probe contains a C:T mismatch with respect to the *C. glabrata* target DNA, located in the middle of the capture probe sequence. The *C. glabrata* capture probe (M) is fully complementary to the *C. glabrata* target DNA.

The probe complexes are attached an electrode surface as described in Example 1. A 294 bp amplicon (SEQ ID NO: 12) of *C. glabrata* target DNA was allowed to hybridize to the probe complex as described in Example 1 in (1) 0.8xSSC; (2) 5xSSC; (3) 5xSSC in the presence of 1.75 µM of a competitor DNA probe [15.1-31] (SEQ ID NO: 8); or (4) 5xSSC in the presence of 2.2 µM of a competitor DNA probe [15.1-31] (SEQ ID NO: 8). The washing, rinsing, and detection steps were carried out as described in Example 1.

Figure 5:
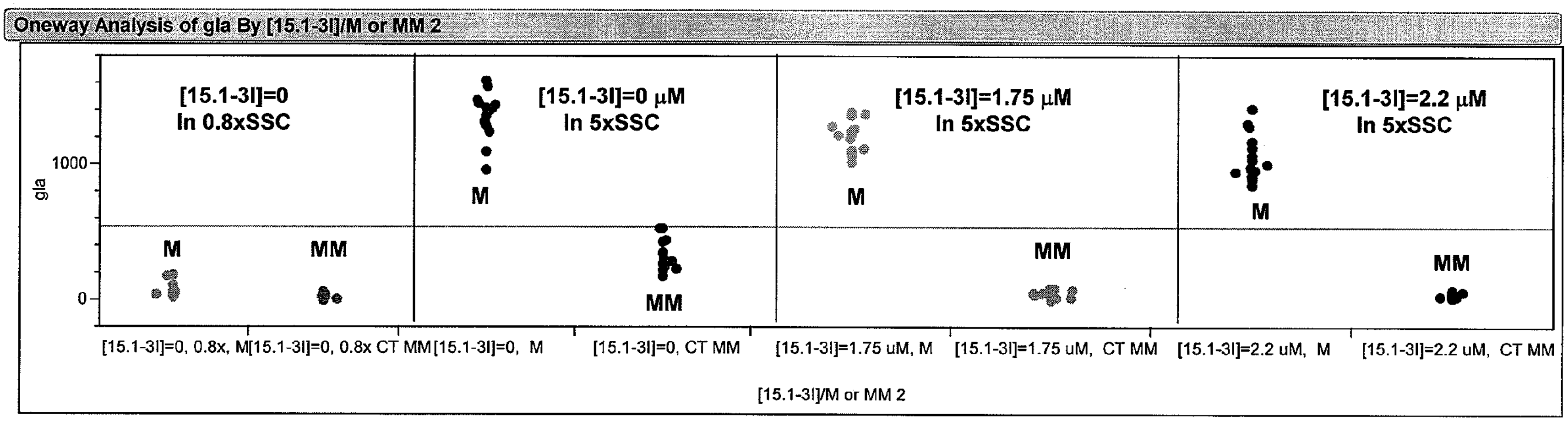
FIG. 5 is a graph of electrochemical measurements reflecting the amount of target sequence (DNA derived from *Candida glabrata*) hybridized to two different probe complexes, M and MM. As indicated, the hybridization reactions were carried out with or without competitor nucleic acids in either 0.8×SSC or 5×SSC. The probe complexes contain identical linker sequences (SEQ NO. 2), and capture probe regions that are either fully complementary (M) or have a C:T mismatch (MM) with the target DNA. The mismatch is located in the middle of the probe.

The results are presented in FIG. 5 and Table 5. The addition of competitor DNA to high salt hybridization conditions in the electrochemical hybridization assay generated a lower signal than when the assay was conducted in the absence of competitor DNA, e.g. 41nA compared to 326nA. Varying the concentration of competitor DNA from 1.75 µM to 2.2 µM did not adversely affect the ability to discriminate target DNA from mismatches.

TABLE 5

| Level | Number | Mean | Std. Dev. | Std. Err. Mean | Lower 95% | Upper 95% |
|---|---|---|---|---|---|---|
| 0.8xSSC (M) | 12 | 73.44 | 56.130 | 16.203 | 37.8 | 109.1 |
| 0.8xSSC (MM) | 12 | 22.74 | 20.036 | 5.784 | 10.0 | 35.5 |

TABLE 5-continued

| Level | Number | Mean | Std. Dev. | Std. Err. Mean | Lower 95% | Upper 95% |
|---|---|---|---|---|---|---|
| 5xSSC (M) no competitor | 14 | 1359.43 | 173.253 | 46.304 | 1259.4 | 1459.5 |
| 5xSSC (MM) no competitor | 14 | 326.81 | 113.012 | 30.204 | 261.6 | 392.1 |
| 5xSSC (M) 1.75 μM competitor | 16 | 1213.21 | 124.120 | 31.030 | 1147.1 | 1279.4 |
| 5xSSC (M) 1.75 μM competitor | 16 | 43.08 | 25.324 | 6.331 | 29.6 | 56.6 |
| 5xSSC (M) 2.2 μM competitor | 16 | 1083.57 | 184.631 | 46.158 | 985.2 | 1182.0 |
| 5xSSC (MM) 2.2 μM competitor | 16 | 41.17 | 17.618 | 4.404 | 31.8 | 50.6 |

To assess the ability to distinguish A:G mismatches to target DNA, the amperometric readings of hybridization reactions between capture probes containing *C. glabrata* or *C. kefyr* sequences, (SEQ ID NOs: 10 and 11 respectively) and *C. kefyr* target DNA (SEQ ID NO: 13) were assessed and compared. The *C. kefyr* (M) capture probe contains a C:T mismatch with respect to the *C. glabrata* target DNA, located in the middle of the capture probe sequence. The *C. kefyr* capture probe (MM) is fully complementary to the *C. kefyr* target DNA.

The probe complexes are attached an electrode surface as described in Example 1. A 294 bp amplicon (SEQ ID NO: 13) of *C. kefyr* target DNA was allowed to hybridize to the probe complex as described in Example 1 in (1) 3×SSC; or (2) 3×SSC in the presence of 2.0 μM of a competitor DNA probe [15.1-31] (SEQ ID NO: 8). The washing, rinsing, and detection steps were carried out as described in Example 1.

Figure 6:
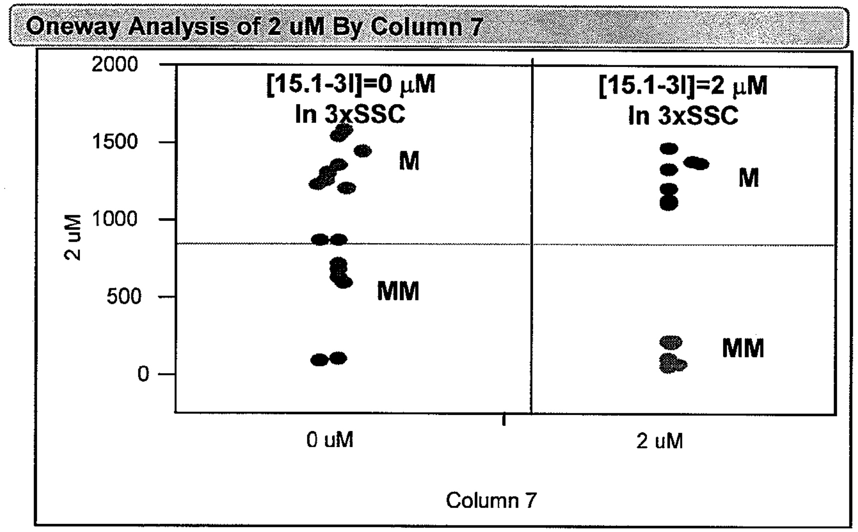
FIG. 6 is a graph of electrochemical measurements reflecting the amount of target sequence (DNA derived from kefyr) hybridized to two different probe complexes, M and MM. As indicated, the hybridization reactions were carried out with or without competitor nucleic acids in 3×SSC. The probe complexes contain identical linker sequences (SEQ NO. 2), and are either fully complementary (M) to the target DNA, or have an adenine to guanine change (MM) resulting in a one base-pair mismatch with the target DNA. The mismatch is located in the middle of the probe.

The results are presented in FIG. 6 and Table 6. The addition of competitor DNA to high salt hybridization conditions in the electrochemical hybridization assay generated a lower signal than when the assay was conducted in the absence of competitor DNA, e.g. 149nA compared to 700nA.

TABLE 6

| Level | Number | Mean | Std. Dev. | Std. Err. Mean | Lower 95% | Upper 95% |
|---|---|---|---|---|---|---|
| 3xSSC (M) no competitor | 8 | 1367.93 | 140.237 | 49.58 | 1250.7 | 1485.2 |
| 3xSSC (MM) no competitor | 8 | 571.18 | 304.228 | 107.56 | 316.8 | 825.5 |
| 3xSSC (M) 2.0 μM competitor | 8 | 1264.75 | 141.040 | 49.87 | 1146.8 | 1382.7 |
| 3xSSC (MM) 2.0 μM competitor | 8 | 149.62 | 71.922 | 25.43 | 89.5 | 209.7 |

Figure 7:
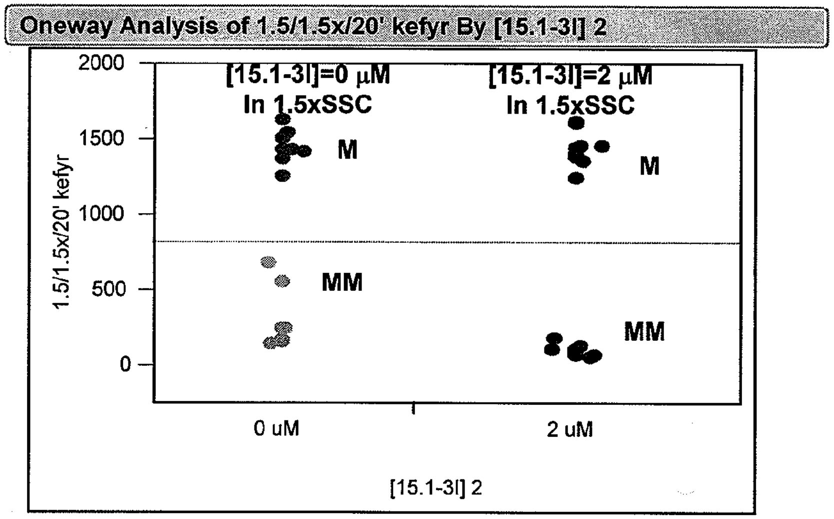
FIG. 7 is a graph of electrochemical measurements reflecting the amount of target sequence (DNA derived from kefyr) hybridized to two different probe complexes, M and MM. As indicated, the hybridization reactions were carried out with or without competitor nucleic acids in 1.5×SSC. The probe complexes contain identical linker sequences (SEQ NO. 2), and are either fully complementary (M) to the target DNA or have an adenine to guanine A:G change (MM) resulting in a one base-pair mismatch with the target DNA. The mismatch is located in the middle of the probe.

To test the ability to discriminate the A:G mismatch described above in lower salt buffer, the experiment described in this example with target DNA from *C. kefyr* was performed in 1.5×SSC in the presence or absence of 2 μM competitor DNA. The results are presented in FIG. 7 and Table 7. The addition of competitor DNA to low salt hybridization conditions in the electrochemical hybridization assay generated a lower signal than when the assay was conducted in the absence of competitor DNA, e.g. 100nA compared to >302nA.

TABLE 7

| Level | Number | Mean | Std. Dev. | Std. Err. Mean | Lower 95% | Upper 95% |
|---|---|---|---|---|---|---|
| 1.5xSSC (M) no competitor | 8 | 1447.42 | 113.389 | 40.089 | 1352.6 | 1542.2 |
| 1.5xSSC (MM) no competitor | 8 | 302.9 | 199.979 | 70.703 | 135.7 | 470.1 |
| 1.5xSSC (M) 2.0 μM competitor | 10 | 1436.06 | 112.504 | 35.577 | 1355.6 | 1516.5 |
| 1.5xSSC (MM) 2.0 μM competitor | 10 | 99.57 | 34.556 | 10.928 | 74.9 | 124.3 |

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific examples and studies detailed above are only illustrative of the invention. It should be understood that various modifications can be made without departing from the spirit of the invention. Accordingly, the invention is limited only by the following claims.

What is claimed is:

1. A method for increasing hybridization efficiency between a capture probe and a target nucleic acid, comprising:

providing a probe complex comprising a capture probe and a linker sequence, wherein said capture probe comprises a complementary region comprising a nucleic acid that is substantially complementary to a target nucleic acid sequence, and wherein said linker sequence is operably linked to said capture probe;

providing a target nucleic acid, wherein said target nucleic acid or a fragment thereof is substantially complementary to said complementary region of said capture probe;

providing a competitor nucleic acid, wherein said competitor nucleic acid comprises a complementary region that is fully complementary to said linker sequence and a universal region comprising at least about two universal bases that can hybridize to A, T, C and G, wherein said universal bases are nucleotide analogs that form fewer hydrogen bonds with naturally occurring nucleotides than between naturally occurring nucleotides, and wherein said universal region is adjacent to the 5' end of said complementary region of said competitor nucleic acid; and contacting said probe complex with said target nucleic acid and said competitor nucleic acid, thereby increasing the hybridization efficiency between the capture probe and the target nucleic acid.

2. The method of claim 1, wherein said universal region comprises at least about 3, 4, 5, or 6 universal bases.

3. The method of claim 2, wherein said universal region consists of about 3 universal bases.

4. The method of claim 1, wherein said at least about two universal bases are selected from the group consisting of deoxyinosine, 3-ntiropyrorole, 4-nitroindole, 6-nitroindole, and 5-nitroindole, or any combination thereof.

5. The method of claim 4, wherein said at least two universal bases are deoxyinosine.

6. The method of claim 1, wherein said linker sequence is about 7 to about 45 nucleotides in length.

7. The method of claim 6, wherein said linker sequence is about 10 to about 20 nucleotides in length.

8. The method of claim 1, wherein said capture probe is about 7 to about 45 nucleotides in length.

9. The method of claim 1, wherein said capture probe is substantially the same length as said linker sequence.

10. The method of claim 1, wherein said competitor nucleic acid can anneal to said linker region under conditions of high salt, wherein said conditions of high salt comprise 5× SSC at about 50-60° C.

11. The method of claim 1, wherein said competitor nucleic acid is provided at a final concentration of about 0.1 μM to about 5 μM.

12. The method of claim 1, wherein said competitor nucleic acid is provided at a final concentration of about 1.5 μM to about 3.5 μM.

13. The method of claim 1, wherein the ratio of the target nucleic acid to the competitor is between about 1:40 and about 1:135.

14. The method of claim 1, wherein the $T_m$ of the capture probe and the universal region of said competitor DNA is approximately the same.

15. The method of claim 1, wherein the $T_m$ of the competitor nucleic acid is greater than the $T_m$ of the capture probe.

16. The method of claim 1, wherein said linker sequence of said probe complex is operably attached to a solid support.

17. A method of increasing the sensitivity and specificity of a nucleic acid hybridization assay, comprising:

providing a capture probe that is substantially complementary to a target nucleic acid sequence in a sample;

providing a competitor nucleic acid that reduces the hybridization efficiency of non-target nucleic acids to said capture probe, wherein said competitor nucleic acid comprises a universal region comprising at least about 2 universal bases at the 5' end of said nucleic acid, wherein said universal bases are nucleotide analogs that form fewer hydrogen bonds with naturally occurring nucleotides than between naturally occurring nucleotides, and; and contacting said capture probe with said sample and said competitor nucleic acid, thereby increasing the sensitivity and specificity of the nucleic acid hybridization assay.

18. The method of claim 17, wherein said capture probe is operably linked to a linker sequence, and wherein said competitor nucleic acid comprises a complementary region comprising a nucleic acid that is substantially complementary to said linker sequence, wherein said complementary region is operably linked to the 3' end of said universal region.

19. The method of claim 17, wherein said universal region comprises at least about 3, 4, 5, or 6 universal bases.

20. The method of claim 19, wherein said universal region consists of about 3 universal bases.

21. The method of claim 17, wherein said at least two universal bases are selected from the group consisting of deoxyinosine, 3-ntiropyrorole, 4-nitroindole, 6-nitroindole, and 5-nitroindole.

22. The method of claim 21, wherein said universal base is deoxyinosine.

23. The method of claim 18, wherein said linker sequence is about 7 to about 45 nucleotides in length.

24. The method of claim 23, wherein said linker sequence is about 10 to about 20 nucleotides in length.

25. The method of claim 17, wherein said capture probe is about 7 to about 45 nucleotides in length.

26. The method of claim 25, wherein said capture probe is about 10 to about 20 nucleotides in length.

27. The method of claim 18, wherein said capture probe is substantially the same length as said linker sequence.

28. The method of claim 18, wherein said competitor nucleic acid can anneal to said linker sequence under conditions of high salt, wherein said conditions of high salt comprise 5× SSC at about 50-60° C.

29. The method of claim 17, wherein said competitor nucleic acid is provided at a final concentration of about 0.1 μM to about 5 μM.

30. The method of claim 17, wherein said competitor nucleic acid is provided at a final concentration of about 1.5 μM to about 3.5 μM.

31. The method of claim 17, wherein the $T_m$ of the capture probe and the universal region of said competitor DNA is approximately the same.

32. The method of claim 17, wherein the $T_m$ of the competitor nucleic acid is greater than the $T_m$ of the capture probe.

33. The method of claim 18, wherein said linker sequence of said probe complex is operably attached to a solid support.

34. The method of claim 17, wherein the ratio of the target nucleic acid to the competitor is between about 1:40 and about 1:135.

* * * * *

SEQUENCE LISTING

```
<160> NUMBER OF SEQ ID NOS: 13

<210> SEQ ID NO 1
<211> LENGTH: 10
<212> TYPE: DNA
<213> ORGANISM: Artificial Sequence
<220> FEATURE:
```

-continued

<223> OTHER INFORMATION: Synthetic oligonucleotide

<400> SEQUENCE: 1
aaaaaaaaaa 10

<210> SEQ ID NO 2
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 2
acagttcctg catg 14

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
gtaagttcga agaattgtt 19

<210> SEQ ID NO 4
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 4
ccaagaacga cccaccaaag gctgctgctt ctttcaacgc taccgtcatt gtcttgaacc 60
acccaggtca aatctctgct ggttactctc cagttttgga ctgtcacacc gcccacattg 120
cttgtaagtt cgaagaattg ttggaaaaga acgacagaag atccggtaag aagttggaag 180
actctccaaa gttcttgaag tccggtgacg ctgctttggt taagttcgtt ccatccaagc 240
caatgtgtgt cgaagctttc tccgactacc caccattggg tagattcgct gtca 294

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 5
agttggtaga agcctc 16

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 6
agttggtaga agcttc 16

<210> SEQ ID NO 7
<211> LENGTH: 266
<212> TYPE: DNA
<213> ORGANISM: Artificial Sequence -continued
<220> FEATURE:
<223> OTHER INFORMATION: Synthetic oligonucleotide

<400> SEQUENCE: 7
ggttggttac aaccctaaga ctgtgccatt cgttcctatc tctggatgga ayggtgacaa 60
catgattgag gcttctacca actgtccttg gtacaaggga tgggagaagg agaccaaggc 120
tggtaagtcc accggtaaga ctttgttgga ggccattgac gccattgagc cacctcaaag 180
accaaccgac aagccattga gattgccatt gcaagatgty tacaagattg gtggtattgg 240
aacggtgcca gtcggtagag ttgaaa 266

<210> SEQ ID NO 8
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 8
catgcaggaa ctgtt 15

<210> SEQ ID NO 9
<211> LENGTH: 263
<212> TYPE: DNA
<213> ORGANISM: Artificial Sequence
<220> FEATURE:
<223> OTHER INFORMATION: Synthetic oligonucleotide

<400> SEQUENCE: 9
gaaggttggt tacaacccta aggctgttcc attcgttcca atctctggtt ggaatggtga 60
caacatgatt gaagcttcta ccaactgtcc atggtacaag ggttgggaaa aagaactggt 120
aaggttaccg gtaagacttt gttggaagcc attgatgcta ttgaaccacc ttcaagacca 180
actgacaagc cattgagatt gccattgcaa gatgtttaca agattggtgg tattggtact 240
gtggccagtc ggtagagttg aaa 263

<210> SEQ ID NO 10
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 10
acagttcctg catggtaagt tcgaagaatt gtt 33

<210> SEQ ID NO 11
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 11
acagttcctg catggtaagt tcgacgaatt gtt 33

<210> SEQ ID NO 12
<211> LENGTH: 294
<212> TYPE: DNA
<213> ORGANISM: Artificial Sequence
<220> FEATURE:
<223> OTHER INFORMATION: Synthetic oligonucleotide -continued

```
<400> SEQUENCE: 12

ccaagaacga cccaccaaag gctgctgctt ctttcaacgc taccgtcatt gtcttgaacc     60

acccaggtca aatctctgct ggttactctc cagttttgga ctgtcacacc gcccacattg    120

cttgtaagtt cgaagaattg ttggaaaaga acgacagaag atccggtaag aagttggaag    180

actctccaaa gttcttgaag tccggtgacg ctgctttggt taagttcgtt ccatccaagc    240

caatgtgtgt cgaagctttc tccgactacc caccattggg tagattcgct gtca          294


<210> SEQ ID NO 13
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 13

ccaagaacga cccaccaaag gctgctgctt ctttcaacgc cactgttatc gtcttgaacc     60

acccaggtca aatctctgct ggttactctc cagttttgga ttgtcacact gctcacattg    120

cttgtaagtt cgacgaattg ttggaaaaga acgacagaag atccggtaag aagttggaag    180

actctccaaa gttcttgaag tctggtgacg ctgctttggt taagttcgtt ccatctaagc    240

caatgtgtgt tgaagcattc tctgactacc caccattggg tagattcgct gtca          294
```